United States Patent

Ward

[11] 3,958,120
[45] May 18, 1976

[54] RADIOGRAPHIC INSPECTION OF STEAM GENERATOR TUBES

[75] Inventor: Charles Theodore Ward, Chattanooga, Tenn.

[73] Assignee: Combustion Engineering, Inc., Windsor, Conn.

[22] Filed: Nov. 12, 1973

[21] Appl. No.: 415,042

[52] U.S. Cl. .............................. 250/321; 250/320; 250/491
[51] Int. Cl.² ........................................ G03B 41/16
[58] Field of Search .......... 250/320, 321, 323, 358, 250/360, 490, 491

[56] References Cited
UNITED STATES PATENTS

| 2,412,174 | 12/1946 | Rhoades | 250/321 |
|---|---|---|---|
| 2,501,174 | 3/1950 | Herzog | 250/360 |
| 2,702,864 | 2/1955 | McKee | 250/360 |
| 3,182,197 | 5/1965 | Putnam et al. | 250/321 |
| 3,629,583 | 12/1971 | Plasser et al. | 250/360 |
| 3,686,932 | 8/1972 | Ries et al. | 250/321 |
| 3,872,310 | 3/1975 | Charlton et al. | 250/358 |

FOREIGN PATENTS OR APPLICATIONS 2,307,833  8/1973  Germany

Primary Examiner—Archie R. Borchelt
Assistant Examiner—B. C. Anderson
Attorney, Agent, or Firm—Robert L. Olson

[57] ABSTRACT

Apparatus and a method for the inspection of tubes in a steam generator include a film-bearing cassette probe insertable into a target tube to a predetermined region to be inspected and a source of radiation, preferably a radioisotope, insertable into a tube adjacent said target tube to a position therealong laterally adjacent the region to be inspected on said target tube. The cassette probe is sufficiently flexible to transit regions of tight tube curvature.

8 Claims, 12 Drawing Figures

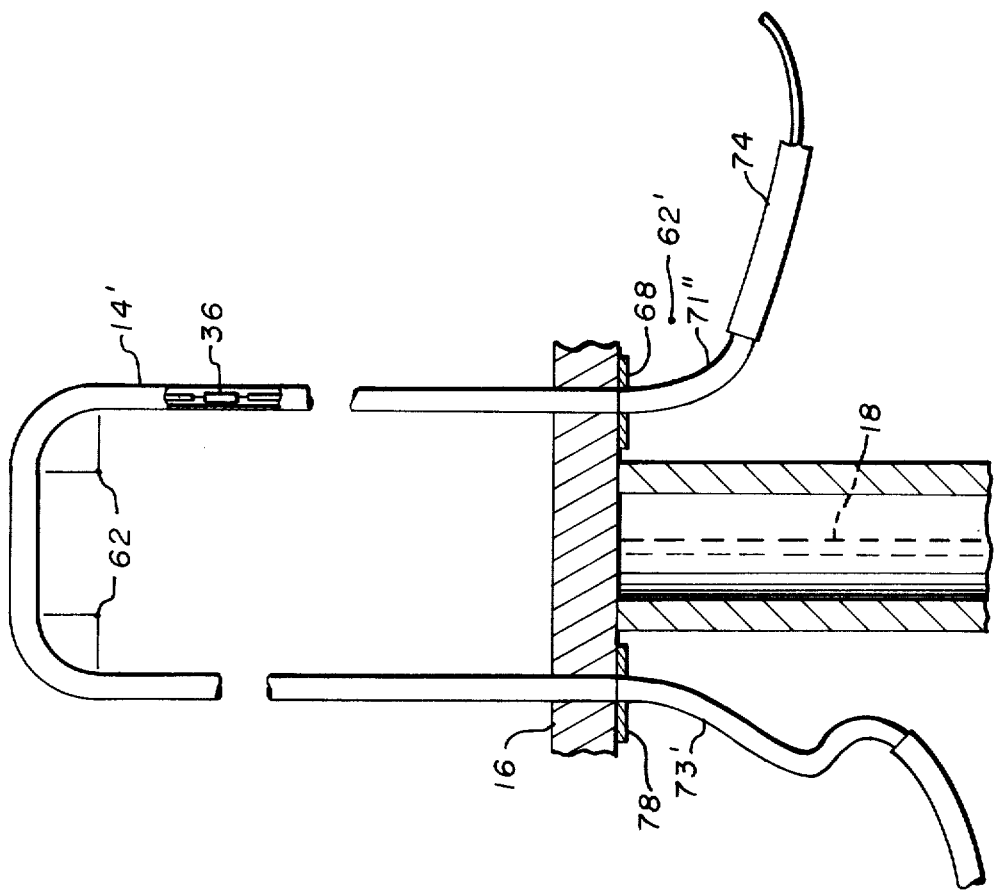
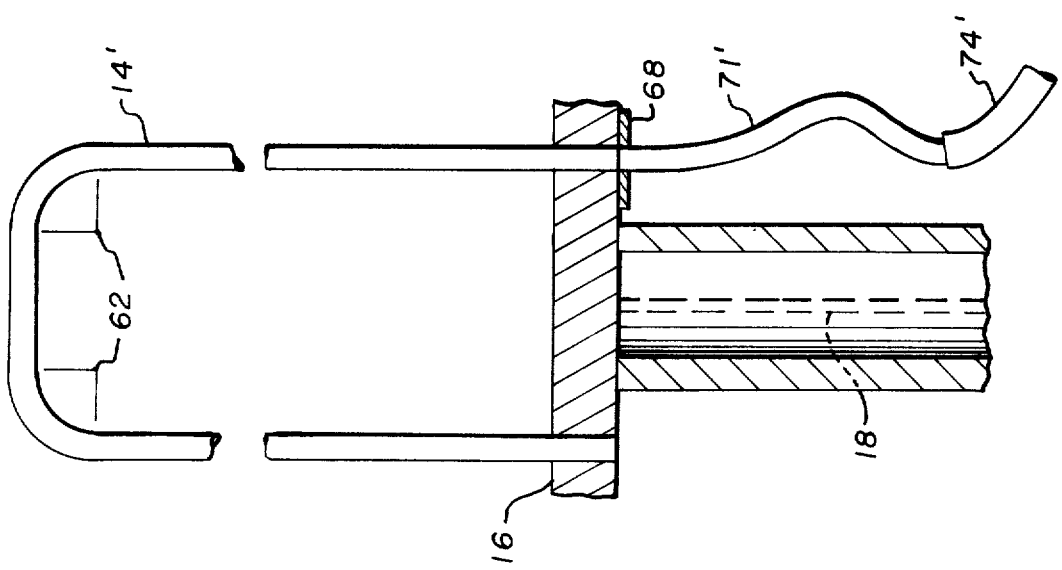
FIG. 12
FIG. 11

RADIOGRAPHIC INSPECTION OF STEAM GENERATOR TUBES

BACKGROUND OF THE INVENTION

The invention relates to a method and apparatus for inspecting tubing. More specifically, the invention relates to the use of radiography for nondestructively inspecting tubes in a nuclear steam generator.

From time to time during the life of a nuclear steam generator, it may be desirable to nondestructively inspect portions of the many fluid conducting heat exchanger tubes which comprise a major part of the generator. Because of the closely packed arrangement of the tubes in the steam generator tube bundle and the general inaccessibility of the tube exteriors, the inspections are generally conducted from within a tube. Such inspection techniques have heretofore typically relied on ultrasonic and/or eddy current techniques to detect and generally identify pitting, cracking, and/or erosion of, and/or crud buildup on the tube. While these techniques have been quite useful in generally locating such aberrations, they have been unable to provide some of the information desired about the aberrations. More specifically, it may be desirable to know precisely the orientation shape and definition of cracks and the like in the tube walls. Such information is useful in evaluating the seriousness of the problem and may be useful analytically in establishing the nature, and thus possibly the cause, of the aberration, as well as its degree of severity.

SUMMARY OF THE INVENTION

According to the invention there is provided a method and apparatus for radiographically inspecting the heat exchanger tubes in a nuclear steam generator. A source of radiation, typically gamma radiation, is remotely positionable within substantially any tube of the steam generator at any position along its length. A radiation responsive recording means, such as a cassette containing a film responsive to the radiation, is remotely positionable in any tube of the steam generator at any position along its length. A particular tube is selected for inspection; the radiation source is inserted into a tube adjacent thereto, to a position therealong which is laterally adjacent a predetermined target location in the tube to be inspected; and the film cassette is inserted in the tube to be inspected and moved to the position therealong which is preselected as the target. Following exposure of the film in the cassette, it is removed from the target tube, and is processed and examined to obtain the desired information.

In order to inspect the full circumference of the tube at the target location, the above-described operation may be repeated, each time locating the radiation source in a different tube at a different angular position about the circumference of the target tube. Further, the film will preferably be replaced between each different exposure.

The support cartridge for the film is preferably cylindrical and can be made resiliently bendable to easily transit the curved portions of a tube. At times the film should preferably be of a size and shape such that it extends only part way around the cartridge when the application requires the cassette assembly to transit a bend. The film and cartridge are angularly azimuthally oriented to place the film between the radiation source and the cartridge, and directly facing the radiation source.

BRIEF DESCRIPTION OF THE DRAWINGS

FIG. 11 is an elevational view of a portion of the steam generator interior showing a modification of the tube extension of FIG. 1.

FIG. 12 is an elevational view of a portion of the steam generator interior showing a further modification of the tube extension arrangement of FIG. 1.

DESCRIPTION OF THE PREFERRED EMBODIMENT

Figure 1:
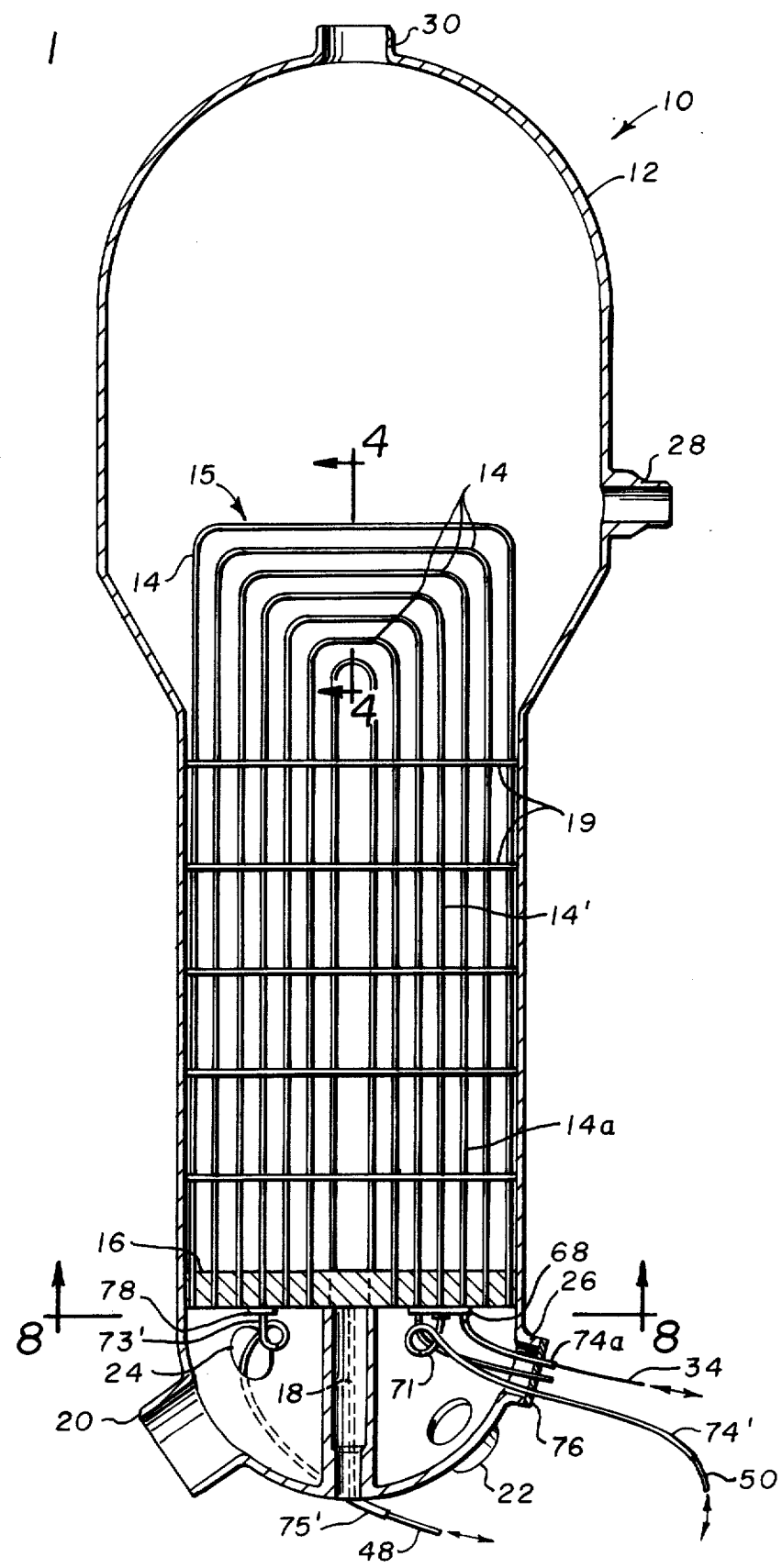
FIG. 1 is vertical sectional view of a steam generator taken through the center thereof parallel the rows of tubes therein with the probe and radiation source inserted into a pair of tubes.

Referring now to FIG. 1, there is depicted a nuclear steam generator 10 including a vessel 12 having a large number of heat exchange tubes 14 supported therein and terminating at one or both ends in a tube sheet 16. Tube sheet 16 is about 12 feet in diameter and is supported by vessel 12. In the steam generator 10 depicted, tubes 14 are shaped as an inverted "U" with the two legs extending vertically upward from tube sheet 16 on opposite sides of the vertical midplane of the steam generator, and the nexus connecting the two legs at their upper ends either through two spaced 90° curved bends or a single 180° bend. Additional lateral support and alignment of tubes 14 may be provided by an eggcrate type grid 19 at various positions along the length of the tubes. Tubes 14 are hollow and circular in cross section and their ends extend through cylindrical bores extending vertically through the horizontal tube sheet 16. Tubes 14 are secured to the tube sheet 16, as by welding. Typically, a tube 14 has an outside diameter of about ¾ inch and an inside diameter of ⅝ inch and is formed of corrosion resisting alloy.

Tubes 14 may number between 7,000 and 9,000 and are in a bundle 15 which is comprised of more than 100 side-by-side parallel rows of tubes, each row including from 1 to 50 or more tubes in nested arrangement, a typical such row appearing in FIG. 1. The nesting of tubes 14 in a row is accomplished by making the vertical and horizontal portions of a tube near the midplane of the generator of particular lengths and progressively increasing these lengths for those tubes further away from the midplane.

The vertical run of a leg of a short tube 14 might be 19 to 23 feet and the nexus between the pair of legs is formed by a section of tube bent 180° about a 2-½ inch radius. The vertical run of a leg of a long tube 14 might be 23 to 29 feet and the nexus between the pair of legs formed by a horizontally extending section of tubing about 7 to 11 feet long having a 90° bend of about 10 inch radius on each end.

Figure 8:
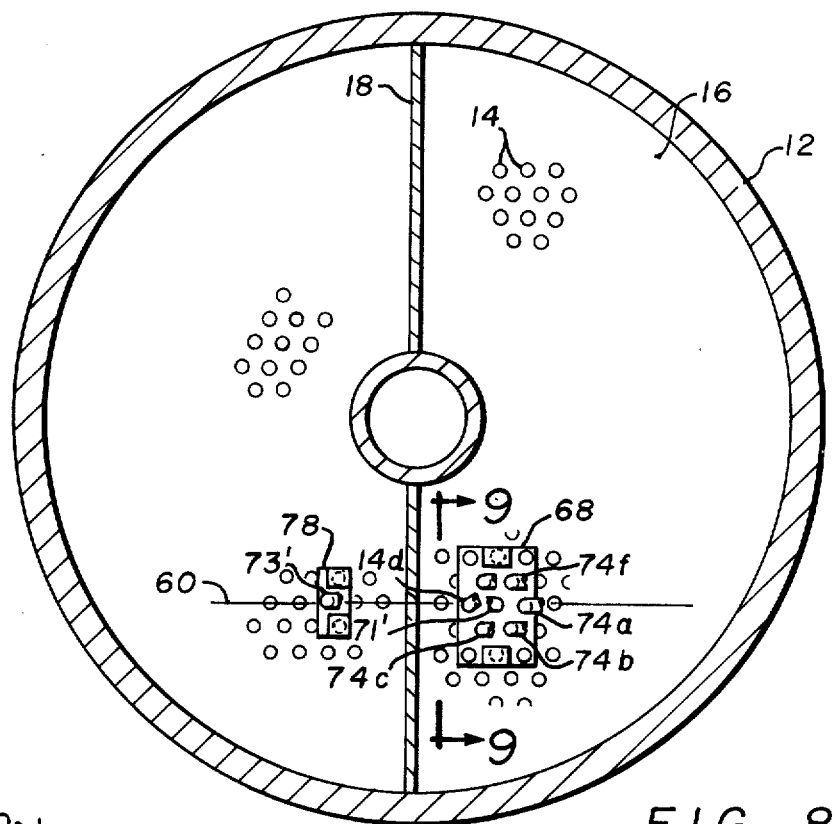
FIG. 8 is an underside view of the tube sheet of FIG. 1 taken along line 8—8 therein to show the cable guiding and aligning fixtures.
Figure 4:
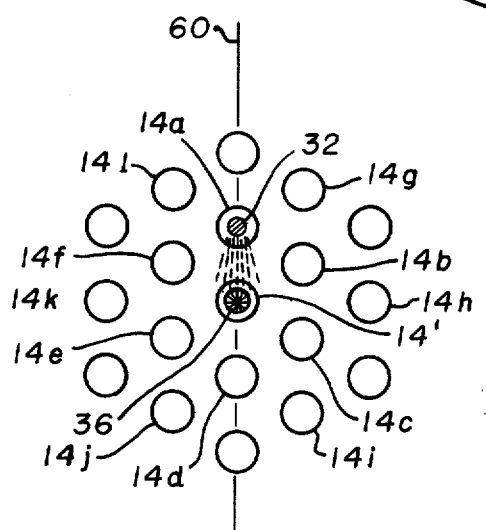
FIG. 4 is a sectional view of a portion of the tube bundle taken normal to the centerline of the tubes along line 4—4 of FIG. 1.
Figure 6:
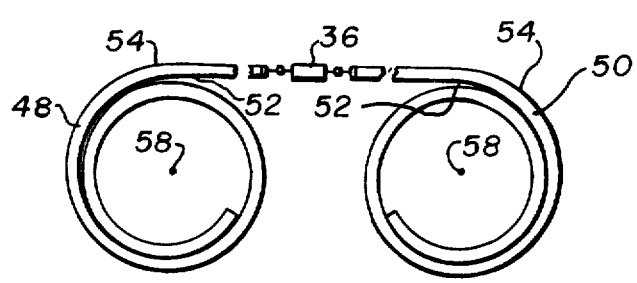
FIG. 6 shows the cables having the resilient naturally curved cast used to angularly align and longitudinally position the probe within a tube.

While the various rows of tubes are parallel one another, adjacent rows may be aligned in one design, or offset in another design, the latter being described and depicted herein, as in FIGS. 4 and 8. The tubes 14 of one row are offset relative to the tubes in the rows on either side of it by an amount which is ½ the center-to-center pitch between tubes in a row. In this embodiment, the center-to-center pitch is 1 inch. This arrangement results in the pattern seen in FIGS. 4 and 8, in which six tubes 14 are approximately equiangularly and equidistantly spaced about any particular tube. This pattern holds true for most of the tube bundle 15, the exceptions of course occurring about the perimeter of the bundle.

Tube sheet 16 is fixedly positioned some 5 feet above the lower end of vessel 12. A divider plate 18 extends from tube sheet 16 to the bottom of vessel 12 along the midplane to sealingly divide the lower end of vessel 12 into an inlet side and an outlet side, respectively communicating with opposite ends of tubes 14. A fluid inlet nozzle 20 provides primary fluid entry to vessel 12 and tubes 14 on one side of divider 18. One or more fluid outlet nozzles 22 provides egress of primary fluid from the tubes 14 and vessel 12 on the other side of divider 18. A manway 24 allows human access to the primary inlet side of vessel 12 tube sheet 16 and a manway 26 allows similar access to the primary outlet side. Vessel 12 also includes a feedwater inlet 28 and a steam outlet nozzle 30 on the secondary side of steam generator 10.

Generally an eddy-current and/or ultrasonic inspection of one or more tubes 14 will be conducted, particularly if certain tubes are felt to be leaking or might have various weaknesses. If some aberration, indicating possibility of a crack or wall corrosion or the like is detected, its longitudinal position along the tube 14, and if possible, its angular position about the tube centerline are noted. Then, according to the invention, radiographic inspection means are employed to obtain a well defined pictorial representation of the shape and geometry of the aberration.

The radiographic inspection means comprise a source of radiation, for instance gamma radiation, insertable into a tube 14 to a position therealong and means responsive to the radiation insertable into another tube to a position therealong for recording any images resulting from the radiation following its passage through the tube walls.

The radiation source is preferably a "pill" or capsule 32 of a radioisotope, such as iridium, cobalt, ytterbium, thulium, gadolinium, thorium, or the like, which emits gamma radiation capable of passing through the wall of the tube containing the source and also the wall of the tube containing the recording means. For example pill 32 may be a piece of iridium 192 having a strength of 10–13 curies and enclosed in a small stainless steel housing. Pill 32 is affixed to the end of a long cable 34 which is sufficiently rigid to permit it to be pushed or driven into a source guide conduit, not shown, inserted within tube 14, but is also flexible enough to follow the contour of the tube. The special steel cable commonly used in standard radiographic practice is satisfactory. Cable 34 is sufficiently long to permit pill 32 to be moved to any position along the length of the longest tube, preferably when introduced from only one end of tube 14, but at least when introduction from either end is possible. Cable 34 may be advanced and withdrawn by a conventional cable-feed mechanism, not shown. Pill 32 is withdrawn into and kept within a shielded container when the pill is fully retracted in accordance with standard industry practice. The source guide conduit is a blind-end tube of Nylon which presents cable 34 and pill from contacting the interior surface of a tube 14. The blind end of the source guide conduit is positioned at the preselected longitudinal position in tube 14 and pill 32 is then positioned by advancing cable 34 until the pill contacts the blind end.

The radiation responsive recording means preferably comprise a radiographic or photographic film bearing cassette or probe 36, seen in FIGS. 3–7. Probe 36 comprises a cylindrical, hollow form or cartridge 38 of a resiliently flexible material, such as elastomer tubing, supporting a piece of slow-speed photographic or a radiographic film 40. A support spine 41 having a longitudinally extending center wire or cable and wire ribs extending radially therefrom extends through cartridge 38 and is concentric therewith. The wire ribs of spine 41 are sufficiently numerous, long and rigid to snugly engage the interior wall of cartridge 38 and prevent relative longitudinal and rotational motion therebetween for the frictional and other forces encountered during use. Alternatively, the ends of the cartridge body and support spine may be rigidly affixed by other means such as end fittings to prevent rotational or longitudinal slippage during use.

Cartridge 38 may be about 3 to 4 inches in length and supports a sheet of film 40 on the outer surface thereof. Film 40 may be Kodak 7302 Fine Grain Positive film or one of several radiographic film grades. This film may be selected to have a relatively slow speed to prevent fogging by background radiation in steam generator 10, after operation in a nuclear steam generating system. Film 40 is preferably in the form of a strip extending most of the length of cartridge 38, buy may be only part way there around, for instance 180° when used such as to transit a bend in tube 14'. Film 40 should remain as close to the inside surface of the tube 14 being inspected as possible; however it may tend to bend and possibly be damaged when transiting the bends in the tubes 14 if wrapped entirely around cartridge 38, thus the partial wrap.

An intensifying screen 42, of lead or other material, may cover the outer surface of or completely envelop film 40 in a manner well known in the art of radiography. Screen 42 is optional, its use being determined by the type and intensity of source pill 32, the type of film, and the workpiece in a manner well understood in the art of radiography. Such a screen is sometimes utilized in the preferred embodiment.

The film 40 (and screen 42) may be secured to cartridge 38 and shielded from exposure to light by light-opaque tape 44 wound tightly around the film and cartridge from end to end. A further seal against abuse, moisture, contamination, etc., may be provided by an envelope 146 of heat-shrink material or the like about the cartridge, film and tape. This combination provides a probe 36 having an outside diameter which may be only slightly less than the inside diameter of a tube 14, for instance 0.6 inches, to permit close, but smooth, passage therewithin.

Cartridge support spine 41 extends beyond the end, or ends, of cartridge 38, through envelope 46, sufficiently to permit a connection to be made between it and a cable at one, or preferably both, ends. The form of connection and the nature of the cable or cables attached thereto will be discussed more thoroughly below. Suffice it to say here, that cables 48 and 50 are attached to opposite ends of spine 41 of probe 36 to propel it within a tube 14, by pushing and/or pulling the cables from beyond the ends of tubes 14. Cables 48 and 50 may each be long enough to extend the full length of the longest tube 14 and the distance to and somewhat beyond a manway 24 or 26. Guide tubes, to be described more thoroughly below, extend between the tube sheet 16 and one or both manways 24 and 26 to facilitate remote introduction of a cable 48 or 50 to a particular tube 14.

To inspect any particular tube 14' which has been previously inspected ultrasonically or by eddy current techniques, and more particularly to inspect a particular location along its length, radiation source or pill 32 is introduced to the end of another tube, for instance 14a in FIGS. 1, 2, 4 and 5, which is generally close to tube 14'.

Tube 14a can be immediately adjacent tube 14' or can be one or more tubes spaces away such that one or more additional tubes are in the line-of-sight path between these two tubes. Pill 32 is moved within the tube 14a to a position therealong which is laterally adjacent the longitudinal location to be inspected in tube 14'. This is determined by measuring the extent to which cable 34 and its source guide conduit are inserted in tube 14a.

Subsequently, film-carrying cassette probe 36 is introduced to tube 14' at one end thereof and is propelled within the tube to the location therealong selected for inspection. While the propelling and positioning of probe 36 might be effected by a single cable, as in the case of pill 32, it is preferred for reasons to become evident hereinafter to use a pair of cables 48 and 50 to propel and position probe 36. One of cables 48 and 50 is introduced to one end of tube 14' and is pushed therethrough until it exits the other end of the tube and can be grasped, manually or mechanically, and pulled further until the probe 36 has been drawn into the tube to the location therealong preselected for inspection. This position is determined by the length of cable 48 and/or 50 inserted into tube 14'. This insertion of the probe 36 is done rapidly to reduce exposure effects of radiation on the film while in transit. It will be appreciated that probe 36 might be inserted and positioned in tube 14' prior to the insertion and positioning of pill 32 in another tube 14, particularly if the steam generator 10 has not been previously operated and irradiated.

The probe is allowed to remain stationary at the particular inspection location for sufficient time to expose film 40 to gamma radiation from pill 32. This exposure is sufficient to result in the formation of an image on the film 40 of the target tube wall existing between the film and the pill. In essence, the sharpest and best defined images appearing on film 40 will result from aberrations or flaws in the wall of tube 14' immediately adjacent the film, though a flaw in the wall of tube 14a or other intervening tubes might create a fuzzy and weak image also. For the film cassettes and radiation sources described herein, probe 36 is typically allowed to remain at the inspection location for about 1/10 to 10 or more minutes and is then quickly withdrawn from tube 14' and steam generator 10.

Figure 5:
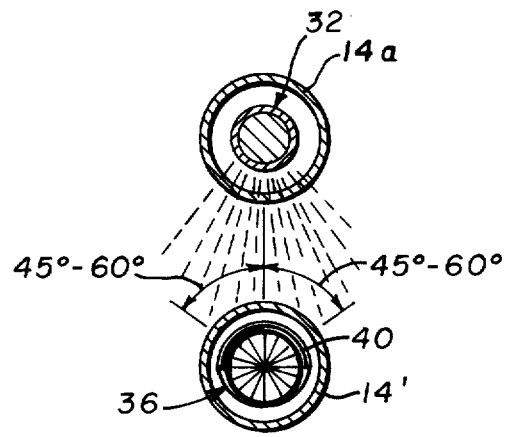
FIG. 5 is an enlarged view of selected tubes in FIG. 4 showing the angular relationship between the radiation source and the probe film relative to the centerline of the probe and tube.

This operation results in the radiographic inspection and recording of the features of an arc portion of tube 14' about its center line or axis, that arc portion being limited by the angular coverage of film 40 (about 180°) and the region thereof irradiated by pill 32, as seen in FIGS. 4 and 5. Typically, the angular extent of optimum inspection coverage for a single positioning of probe 36 and pill 32 is between about 45° and 60° to each side of a line extending between centers of tubes 14' and 14a and relative to the center of tube 14'. This of course permits inspection of only ¼ to ⅓ of the circumference of tube 14' with a single installation of probe 36 and pill 32. This may be sufficient in some cases.

In other cases, however, it may be desirable to inspect the entire circumference of tube 14' at the selected longitudinal location. In such case, the previously described procedures are repeated, inserting the pill into a tube 14b angularly displaced from tube 14a relative to tube 14', inserting probe 36 into tube 14' to the inspection location such that film 40 is substantially centered about a line extending between the centers of tubes 14' and 14b, removing probe 36 from tube 14' and removing pill 32 from tube 14b. This procedure may be repeated for each of tubes 14c, 14d, 14e and 14f which are angularly displaced about the tube 14'. Each of the above alphabetically subscripted tubes 14 is displaced about 60° from the one before it, relative to tube 14'. It might be possible to get adequate coverage using but three of the tubes, for instance tubes 14a, 14c, and 14e.

Alternately, if slightly different angular views are desired of tube 14' from those provided from tubes 14a through 14f, pill 32 might be positioned, sequentially, in one or more of tubes 14g through 14L. Tubes 14g through 14L are spaced from tube 14' twice the distance of and are shifted, angularly, about 30° from tubes 14a through 14f. Tubes 14g through 14L each have a partially unimpeded line-of-sight view of tube 14'. Alternatively, it may be desirable to position pill 32 in other tubes further away from tube 14' such that one or more intervening tubes will be within the radiation path to tube 14'.

Consideration will now be given to the means utilized to facilitate insertion of pill 32 and probe 36 into their respective tubes 14 and, more importantly, the means and technique for accurately controlling the angular or azimuthal orientation of probe 36 relative to the tube 14 in which it is inserted. Control of the azimuthal or angular, orientation of probe 36 is desirable in radiographic inspection where the film 40 does not completely encircle cartridge 38. It is desirable to be able to predetermine or control the azimuthal orientation of cartridge 38 at the inspection location in order to place film 40 directly facing the radiation source and in the path of the gamma radiation penetrating and passing through the wall of a tube 14'. As used herein relative to probe 36, the terms "angular orientation" and "azimuthal orientation" are synonymous and relate to the orientation of any point on probe 36 about its centerline and relative to a surrounding tube, such as 14'.

Through use of elongated alignment means having a resilient naturally curved cast thereto and connected to one or both ends of a probe, such as cassette probe 36, it has been found possible to control the angular orientation of the probe if it, or more precisely the alignment means, is caused to transit a curved length of the tube or other conduit through which it moves.

According to the preferred embodiment of the invention at least one, and preferably both of the probe-propelling cables 48 and 50 exhibit a naturally curved cast or cast and helix. Stated another way, cables 48 and 50 are elongated members, the axis or centerline of each tending to coil or curl substantially into a circle or helix when no external restraining forces are applied thereto. This property is exhibited by a variety of elongated members. For instance, various plastic tubings, coiled metal wire and metal tubes might develop this resiliently curved cast or cast and helix during the forming process which might include extrusion or drawing or the like. Alternately, this resilient naturally curved cast or cast and helix might subsequently be imparted to a straight metal rod or tube, as by bending it around a circular form in the nature of forming a spring or coil. Such material would of course exhibit a degree of resiliency or springiness which would allow it to be straightened somewhat and then return to the curved cast or cast and helix when the straightening forces are removed.

A particularly good example of a cable having the above properties and that used in the preferred embodiment for cables 48 and 50, is one comprising hollow plastic tubing, for instance a plastic such as nylon. Both cables 48 and 50 are rather long lengths, up to 120 feet, of nylon tubing having a naturally curved cast thereto and, typically having an outside diameter of about ¼ inch to ⅝ inch. The nature of this cast is such that cables 48 and 50 tend to form circular coils when external forces are absent as in FIG. 6. With such characteristics, there exists an imaginary line, or inner arc 52, along the side of each cable 48 and 50 closest to the imaginary centers about which they naturally curve and there is another imaginary line, or outer arc 54, along the opposite side of each cable 48 and 50 most remote from their centers of curvature. These arcs 52 and 54 parallel the axes or center lines of each cable 48 and 50 on opposite sides thereof and lie in the plane 56 which extends from the center of natural curvature of the cable through the longitudinally extending axis or centerline thereof. These imaginary centers of curvature are indicated as 58 in FIGS. 6 and 7 and lie in plane 56 referred to above, that plane being generally parallel the plane of the paper.

Figure 2:
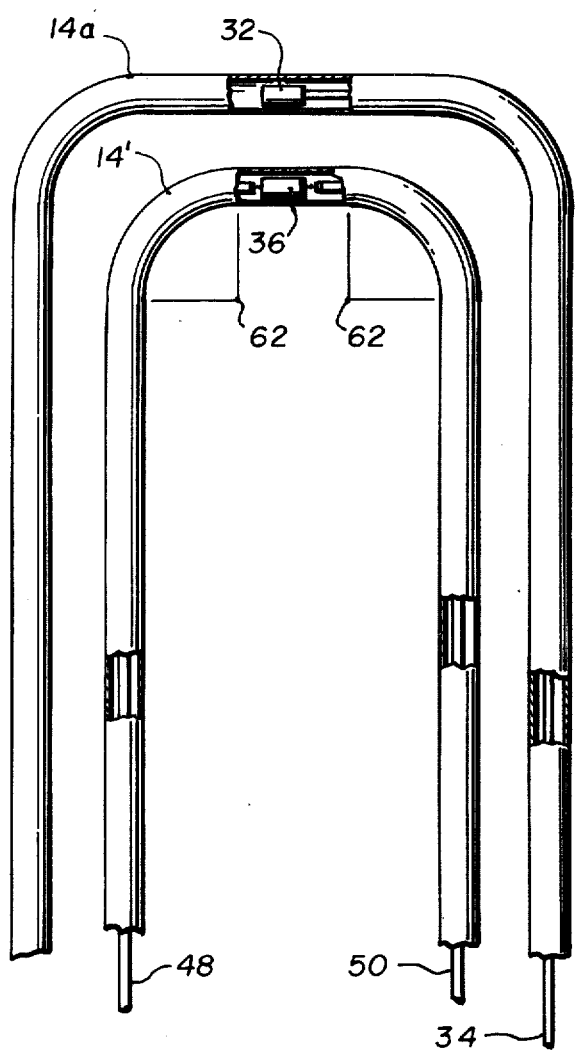
FIG. 2 is a view of selected tubes of FIG. 1 with parts of the tubes cut away to show the relative longitudinal positionings of the probe and radiation source therewithin.

It has been found that when a cable such as 48 or 50 having this natural cast or curvature is inserted into a conduit which is curved along its length, or includes curved sections along its length as the "U" tubes 14, the plane 56 of cable curvature tends to align itself and be coincident with the plane 60 of conduit or tube 14' curvature. In FIG. 2, plane 60 is parallel the plane of the paper, extends through the centerline of tube 14' and includes centers of curvature 62 or tube 14'. More importantly, the alignment or coincidence of planes 56 and 60 occurs with the centers of natural curvature 58 of cables 48 and/or 50 to the same side of the cables and tube 14' as the centers of curvature 62 of the "U" tube. In other words, a cable 48 or 50, upon transiting a curved section of tube 14 will orient itself to one, and only one, predeterminable angular or azimuthal orientation relative to the tube. This is thought to be due to the cables seeking the path of "minimum work" or of " minimum imparted strain energy" due to their elastic deformations.

The natural outer arc 54 of a cable 48 or 50 will be immediately adjacent the comparable outer arc of a tube 14 and the natural inner arc 52 will of course be immediately adjacent the comparable inner arc of the tube. This relationship exists at least along the region of coextensivity of cable 48 and/or 50 and a curved length of tube 14. If no twisting or torsional forces are applied along the length of cable not within a curved section of tube 14, that portion of the cable will also adopt the same angular orientation to the tube in which it extends.

Figure 3:
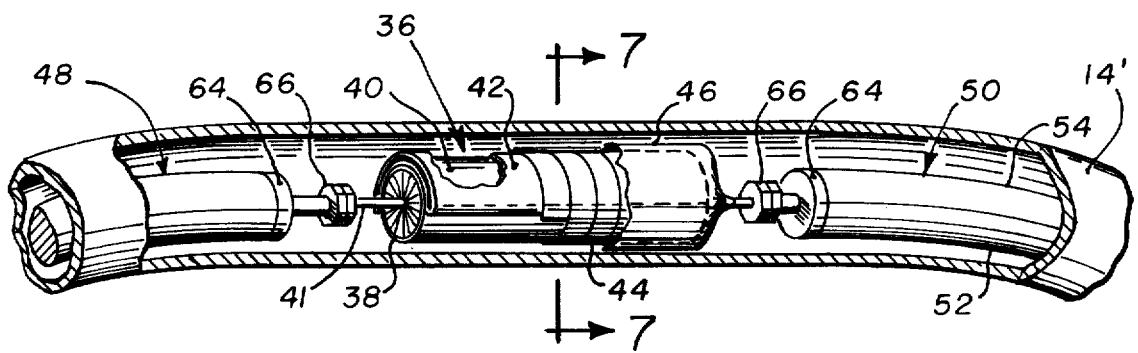
FIG. 3 is an enlarged view of the cutaway section of a tube in FIG. 2 showing the probe in greater detail.

Because of this characteristic of cables which have a curved cast, probe 36 may be nonrotatably affixed to one or both of cables 48 and 50 and its angular rotational orientation within a tube 14 will generally conform to that of the cable at their juncture. As seen in FIG. 3, a cap 64 is nonrotatably affixed to an end of each of cables 48 and 50, as by crimping or bonding it thereto. Spine 41, which is substantially coaxial with probe 36, is nonrotatably affixed at each end to caps 64, as by engaging locking nuts 66, positive clamps, or the like. This arrangement results in film 40, cartridge 38, and cables 48 and 50 being nonrotatably fixed relative to one another during an operation. Probe 36 will also be cut by plane 56 passing through its axis, as seen in FIG. 7 and will include a longitudinally extending line 54' radially outward of spine 41 having the same angular relationship thereto an outer arc 54 of the cables and another longitudinally extending line 52' radially outward of the spine and having the same angular relationship thereto as inner arc 52 of the cables.

Figure 7:
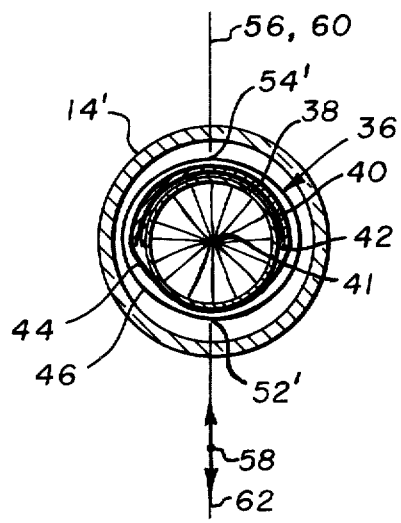
FIG. 7 is a sectional view of the tube and probe of FIG. 3 taken normal to the centerlines thereof along line 7—7 therein to show the predetermined rotational orientation of probe to tube.

FIGS. 3 and 7 show probe 36 and cables 48 and 50 within tube 14' and having their plane of natural curvature 56 coincident with the plane of curvature 60 of the tube, resulting in the aligned planes as indicated by 56, 60. The angular or azimuthal orientation of film 40, relative to the centerline of tube 14' is controlled by the initial angular positioning of the film about the centerline of the cartridge and relative to a reference such as line 54'. In the orientation depicted in FIG. 7, film 40 is centered about line 54'.

If the probe 36 is to support film 40 in a position in tube 14' of FIG. 4 to record an image provided by gamma radiation emitted from a tube, for instance 14c, at a specific angular orientation about tube 14', the operator need only preposition the film at that angular orientation about cartridge 38 which will place it in a line between the cartridge and the source tube 14c.

The above-described means and technique for predetermining and accomplishing the angular orientation of probe 36 at a selected location along a tube having a curved section may be effective when at least part of the naturally curved cable 48 or 50 has transited at least part of the curved length of the tube. If probe 36 is longitudinally close to that portion of a cable which is transiting, or has just transited a curved section of tube 14, it will assume essentially the same angular orientation relative to the tube as the curve-transiting section of cable. If there are no other forces or effects serving to torsionally twist cables 48 and 50, then the probe will assume the same angular orientation relative to tube 14 as the curve-transiting section of the cable, even if it is many feet distant therefrom. This latter situation might occur in a "U" tube 14 if the only pushing-pulling forces applied to cables 48 and/or 50 were directed parallel the vertical runs of the tube, but this may not always be practicable as the cables are led out through manways 24 and 26 at an angle to the "U" tubes and the moving forces are applied outside vessel 12. In such instance, the angular orientation of probe 36 relative to tube 14 might be the predeterminable pattern seen in FIG. 7 only when it is in close longitudinal proximity to, or when it is in the region of or between, the bends or curves at the top of the tube. This limitation to the extent of tube 14 along which probe 36 will assume the above described predetermined angular orientation, while not wholly desirable, may be tolerable if the region of inspection is confined to the longitudinal extent of the tube near, including, or between the bend or bends of the tube nexus.

Otherwise, as the curvature plane of cables 48 and/or 50 might be twisted from the plane of curvature 60 of the tube 14 when they exit from the ends of the tube, they tend also to twist between the tube ends and the region of predeterminable alignment at and between the tube bends. If the extent of this twist is known and varies predictably between the tube bend and tube end, one might calculate or determine the rotational orientation of a probe 36 located therebetween by knowing its longitudinal location and computing the extent of the twist thereat. However, the invention further provides means for avoiding this torsional displacement effect and the need for computation of the extent of twist at the probe when it is along the vertical run of the tube and distant from the bend.

Figure 9:
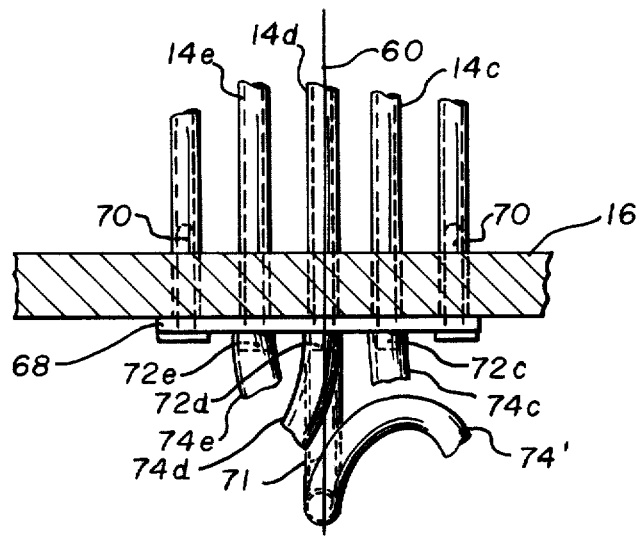
FIG. 9 is an elevational view of the cable guiding and aligning fixtures of FIG. 8 taken along line 9—9 therein.

Referring to FIGS. 1, 8 and 9, there is depicted a fixture plate 68 adapted to be fixedly supported adjacent the undersurface of tube sheet 16, as by expandable fingers 70 which may lockingly engage the inside wall of specific tubes 14 other than those involved in the inspection steps. Alternately, fixture 68 might be carried by or form an integral part of a remotely movable platform such as described in U.S. patent application Ser. No. 384,658 for REMOTELY MOVABLE PLATFORM by C. T. Ward, D. L. Mathis, F. T. Radcliff and R. Vorwerk filed Aug. 1. 1973 and U.S. patent application Ser. No. 384,657 for REMOTELY MOVABLE PLATFORM by C. T. Ward, D. L. Mathis, F. T. Radcliff and E. Ranger filed Aug. 1, 1973. Fixture 68 preferably includes a plurality of vertical, circular openings therethrough positioned to be in registry with the ends of a group of tubes 14, for instance tubes 14' and 14a–f of FIGS. 1 and 4. The openings are of substantially the same diameter as the I.D. of tubes 14. Hollow nipples 72a–f extend downward a short distance from the six openings in registry with tubes 14a–f respectively. Hollow flexible tubular guide conduits 74a–f are affixed at one end to nipples 72a–f respectively, and extend out of vessel 12 through manway 26 to another fixture 76 similar to fixture 68 and supported outside vessel 12.

A curved tube extension 71 extends nonrotatably downward from fixture 68 at the central opening in registry with the end of tube 14'. Extension 71 serves as a curved extension to tube 14' and provides a similar function as the bends in the tube. Extension 71 may be a rigid member having the required curvature, though it may be of a material which has a resilient natural cast thereto, similar to cables 48 and 50. The plane containing the centerline of extension 71 and its center, or centers, of curvature is common with the plane of curvature 60 of tube 14'. Further, the center, or centers of curvature of extension 71 are to the same side of the tubular extension as are the centers of curvature 62 to the tube 14', as viewed in one longitudinal direction. Extension 71 has substantially the same internal diameter as tube 14' and might extend downward from fixture 68 up to about a foot or more. The curved portion of extension 71, if rigid, consists of a bend of approximately 90° or less having a radius of about 5 to 20 or more inches. This curvature generally corresponds in order of magnitude with that of a typical bend in tube 14 in bundle 15.

A flexible tubular guide conduit 74' is affixed at one end to the lower end of extension 71 and extends out through manway 26 to fixture 76, to which its other end is affixed.

It may, for special circumstances, by desirable to position another fixture 78 at the other end of tube 14', particularly if both cables 48 and 50 are used with probe 36 requiring their leadout through both manways 24 and 26 at the same time and if probe 36 must be positioned at any point along tube 14'. Fixture 78 may be similar to fixture 68, though it may be provided with but one opening, in registry with the other end of tube 14', if the cable 34 is long enough to permit radiation pill 32 to be moved to any needed position within tube 14' from a single entry through fixture 68 side.

A tubular nipple in registry with the other end of tube 14' might extend down from fixture 78 and include a flexible guide conduit leading to manway 24 to facilitate introduction and removal of cables 48 and/or 50 to and from tube 14'. If probe 36 is to be used only between a bend of tube 14' and that end of the tube proximate extension 71, then there is no particular need for the nipple and guide conduit of fixture 78 to adhere to the geometrical constraints of extension 71. On the other hand, if the probe 36 is to assume the aforedescribed angular positioning at all points along the length of tube 14', it will be preferable for fixture 78 to include a curved extension similar to that of fixture 68.

Accordingly, a tube extension 73 in registry with the end of tube 14' extends downward from fixture 78 and is of a geometry identical to that of extension 71. The plane of curvature of extension 73 is also the same as for extension 71 and is the plane of curvature 60 for tube 14'. Similarly, the center, or centers, of curvature of extension 73 are to the same side of the extension as are the centers of curvature 62 to the tube 14', when traveling longitudinally in one direction. A flexible tubular guide conduit 75' is affixed at one end to the lower end of extension 73 and extends out through manway 24 to a mount similar to fixture 76 and not shown here.

It will be realized that an extension 71 (73) having the downward and inward geometry described above will encounter interference from divider 18 if the tube 14' is one close to the midline of generator 10. An arrangement of the extension, designated 71', which will avoid interference with the divider is shown in FIG. 11. Extension 71' has a short, shallow arc downward and away from divider 18 near its upper end and continues downward at an angle away from the divider to another arc which is no longer and of greater angular extent and has the same plane and direction of curvature as for the previously described extension 71. The end of extension 71' remote from tube 14' may terminate as shown in FIG. 1 for extension 71 or it may include another short shallow arc away from the divider 18 and to which conduit 74' is attached, as shown in FIG. 11.

While an embodiment has been described and depicted in which extension 71 was a separate, usually rigid member to which conduit 74' was attached, it will be appreciated that conduit 74' might be extended to a short nipple on fixture 68, avoiding the use of extension 71. In effect, conduit 74' would then also serve the function of extension 71 to provide a curved path for probe 36 prior to its entering tube 14'. Of course the constraints on extension 17 will also apply to the end of guide conduit 74' affixed to fixture 68. Conduit 74' will be nonrotatably affixed to fixture 68, or a nipple thereof, such that its plane of natural curvature thereat coincides with plane of curvature 60 of tube 14'. However, the guide conduit 74' may descend or depart from fixture 68 in a gentle, large radius (5–10 feet) helical path which leads out manway 26 to fixture 76, and possibly beyond. This use of extended guide conduit 74' to replace discrete extension 71 may permit operation in a tube 14' located somewhat closer to divider 18 than might be permitted by a rigid extension 71, as in FIG. 1. Care should be taken however, because of the large radius of conduit 74', to insure that the plane of natural cast of cable 48 to coincident with that of guide conduit 74' when the former is introduced to the latter. A similar arrangement of conduit 75' might also be used as a substitute for discrete extension 73.

Returning to the earlier discussion of the tube radiographing technique, it will now be evident that guide conduits 74a–f and nipples 72a–f of fixture 68 facilitate the introduction and removal of radiation source 32 to and from the various tubes surrounding the tube 14' under inspection. If outer circles of tubes, tubes 14g–L or beyond are also to be used to carry and position pill 32, it will be necessary to provide a fixture 68 with corresponding openings, nipples and guide conduits. Further, guide conduits 74' and 75' facilitate the introduction and removal of cables 48 and 50 and probe 36 into and out of tube 14' by an operator or mechanisms positioned outside steam generator 10.

The use of curved extensions to tube 14', such as extensions 71 and 73, permits the angular orientation of probe 36 to be controlled and known along the vertical linear sections of the tube, as well as at the region of and between the bends at the top of the tube. With these extensions, the cable 48 and 50 passing through guide conduit 74' or 75' will become oriented in the single predeterminable angular orientation described earlier upon transiting the curved length of the extension prior to entering tube 14' proper. Correspondingly, probe 36 will be similarly oriented while transiting the curved extension, as earlier described. Thus a probe 36 will assume the aforedescribed predetermined angular orientation prior to entering tube 14' and will retain this orientation throughout its length because the tube bends are in the same plane and direction as the bend in the extension, and because angular displacement errors from torsional or twisting force have been avoided.

If inspection of a "U" tube 14' by probe 36 is to be confined to the vertical linear region between an end of the tube and the bend thereabove, extension 71 (or 73) may be rotated by some amount, typically 180°, from that shown and described above and thereby allow the extension to be positioned on even those tubes immediately adjacent divider 18.

Extension 71'' in FIG. 12 has a center of curvature 62' which is preferably on a side of the extension away from the divider 18. In this instance, center of curvature 62' is in the plane 60 of curvature of tube 14', rotated 180° from that indicated for extension 71 above. In keeping with the teachings of the invention, alignment cables 48 and 50 are intended to have their natural curvatures coincide with the curvatures of the conduit through which they are passing. In this instance, however, cable 48 will have its center of curvature 58 to one side of tube 14', whereas cable 50 will now be required to have its center of curvature 58' to the other side of tube 14' with center of curvature 62' of extension 71''.

In order to avoid torsional forces on probe 36, with this relative configuration of cables 48 and 50, it is necessary to rotate the cable 50 180° relative to cable 48 prior to joining them to opposite ends of the probe. The cables 48 and 50 are then nonrotatably joined to probe 36, as before, but rotated 180° from one another. It will be appreciated that the cable 48 or 50 which is first inserted into the steam generator 10 will necessarily undergo a 180° rotation relative to the conduits in which it is traveling in transiting between the bend of extension 71'' and the bend thereabove in tube 14'. This is no problem however, because that entire cable will be rotated the same amount and become correctly oriented, angularly, with the conduits "downstream" of the preselected longitudinal positioning of probe 36 in tube 14'.

It will be further evident, if extension 71'' is to be used near divider 18, that some provision might also need to be made for the proximity of the other end of tube 14' to divider 18. As seen in FIG. 12, an extension 73', as earlier described, might be used. Alternatively, there may be no specially curved extension provided and instead the angular orientation of cable 48 will be effected by the bends of the "U" tube 14'.

Figure 10:
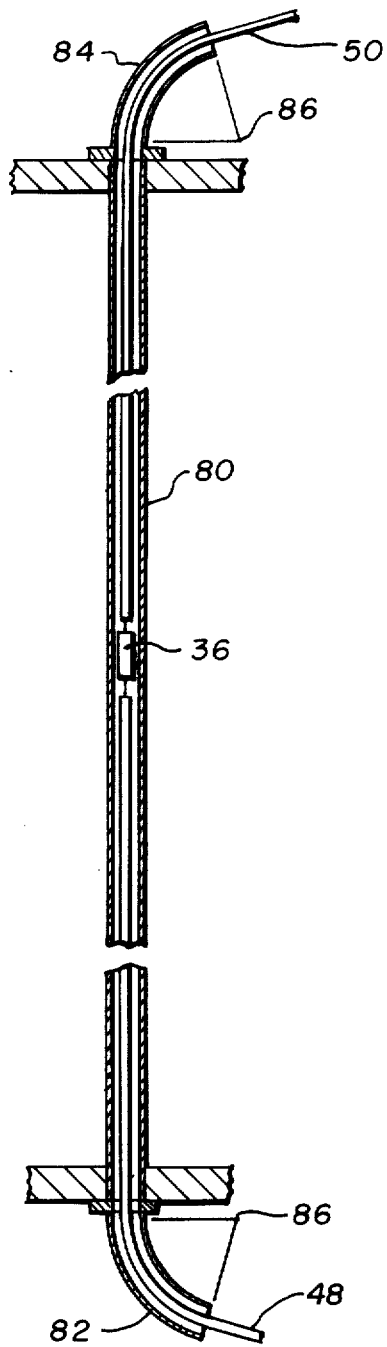
FIG. 10 is a partial sectional view of a straight tube and a pair of curved extensions for the opposite ends thereof showing the cables and probe therewithin.

Brief reference will now be made to the arrangement of FIG. 10 wherein tube 80 may be similar in fuction, diameter and location to tubes 14, but is linear along its entire length rather than curved to form a "U" shape. If naturally curved cables 48 and/or 50 are to push and/or pull probe 36 into tube 80 and the probe is to have a predetermined angular or azimuthal orientation within the tube at a selected longitudinal location, such orientation may be obtained in the manner earlier described through the addition of a curved tubular extension to one, or preferably both, ends of tube 80. Curved tubular extensions 82 and 84 are similar in geometry to extensions 71 and 73. Further, both extensions are supported in registry with the opposite ends of tube 80 by any appropriate means capable of maintaining both extensions in nonrotatable relationship relative to tube 80.

In the embodiment depicted, both extensions 82 and 84 have their centers of curvature 86 and their axes, or centerlines, in the same plane. Further, both centers of curvature 86 are shown in FIG. 10 as being to the same side of tube 80 in the manner of the FIG. 1 embodiment. However, depending on the relative locations of manways, dividers and/or any other constraining structures it may be desirable to rotate extensions 82 and 84 relative to one another about the centerline of tube 80 such that their centers of curvature 86 are not both to the same side of the tube, or in fact, are not even both in a common plant which includes the centerlines of the extensions. In such instance, the cables 48 and 50 will have to be rotated the corresponding angular extent relative to one another when they are joined to probe 36, as described for the FIG. 12 embodiment.

With the above arrangement, a cable, such as 48 or 50, having a resiliently curved cast thereto may be inserted into one end of tube 80 by way of extension 82 or 84. As the cable transits the curved length of the extension, it rotationally orients itself with the extension and the tube 80 beyond as previously described. If no additional torsional forces were applied to the cable, only one curved extension would probably be required to maintain the predetermined rotational orientation of the probe 36 as it transits the length of tube 80. However, if tube 80 is located in an environment similar to that of "U" tubes 14 in which the forces pushing and/or pulling the cables are not only parallel the length of tube 80, it will be preferable to have the curved extensions at both ends of the tube to maintain a constant probe orientation therebetween in spite of other external forces.

For radiographic testing, two or more pills 32 spaced circumferentially around the target location on tube 14' can be used to simultaneously expose a greater proportion circumferentially of the film in cassette probe 36.

The probe so positioned by any of the above-described techniques might be other than one bearing a photographic or radiographic film for radiographic examination. For instance, it might be an eddy current probe or an ultrasonic transducer probe or borescope viewing head or the like, or a metalworking tool or device of a type requiring a particular discrete rotational orientation within the tube at the point of inspection of work performance.

Further, while both the alignment means and the propelling means have been described as all, or part of, a single naturally curved cable, or pair of such cables, it will be appreciated that the propelling means might be a discrete element, as for instance another cable extending within the alignment cable and secured at one end to the probe and having its other end outside the steam generator for receiving a pushing or pulling force.

It will be understood that the embodiment shown and described herein is merely illustrative and that changes may be made without departing from the scope of the invention as claimed.

What is claimed is:

1. In a steam generator having a vessel housing a plurality of open ended tubes arranged laterally adjacent to one another and supported near said ends by a substantially continuous tube sheet extending across said vessel, apparatus for providing a radiographic image of a portion of a said tube comprising:
    a. a radiation responsive image recording means insertable in said tube to be inspected to a first location therealong; and
    b. a source of radiation insertable in another said tube to a position therealong laterally adjacent said first location for emitting radiation between said source and said radiation responsive image recording means.

2. The apparatus of claim 1 wherein said radiation responsive image recording means comprise a photographic medium supported on and carried by a cylindrical cartridge.

3. The apparatus of claim 2 wherein said photographic medium comprises a slow speed photographic film.

4. The apparatus of claim 3 wherein said cartridge is resiliently bendable and said film extends only partway around said cartridge, said part being that closest to said source of radiation.

5. The apparatus of claim 1 wherein said source of radiation emits gamma radiation of sufficient intensity to pass through the walls of both said another tube and said tube to be inspected.

6. In a steam generator having a vessel housing a plurality of open ended tubes arranged laterally adjacent to one another and supported near said ends by a substantially continuous tube sheet extending across said vessel, the method of inspecting a preselected one of said tubes comprising the steps of:
    a. inserting a source of radiation into one of said tubes adjacent said preselected tube to be inspected to a predetermined longitudinal position therealong;
    b. inserting radiation responsive image recording means into said preselected tube to be inspected to a longitudinal position therealong substantially laterally adjacent to said radiation source for exposure thereby;
    c. withdrawing said recording means from said tube; and
    d. withdrawing said radiation source from its said tube.

7. The method of claim 6 wherein said plurality of tubes include at least two tubes substantially parallel said preslected tube to be inspected, each at different angular positions about the axis thereof and wherein said steps of inserting and withdrawing said radiation source are repeated for each of said at least two tubes.

8. The method of claim 6 wherein said radiation responsive recording means comprise a photographic film supported on, carried by, and extending only partially around a cylindrical cartridge and said step of inserting said recording means includes angularly orienting said cartridge within said tube to place said film between said cartridge and said radiation source.

* * * * *